United States Patent [19]

Swithenbank

[11] 4,395,570
[45] Jul. 26, 1983

[54] PREPARATION OF 5-(2-HALO-4-TRIFLUOROMETHYL-PHENOXY)-2-NITROBENZOIC ACID AND SALTS AND ESTERS AND AMIDES

[75] Inventor: Colin Swithenbank, Perkasie, Pa.

[73] Assignee: Rohm and Haas Company, Philadelphia, Pa.

[21] Appl. No.: 321,658

[22] Filed: Nov. 16, 1981

[51] Int. Cl.³ .............................................. C07C 99/00
[52] U.S. Cl. ...................................... 562/435; 560/21; 260/465 D
[58] Field of Search .......................... 560/21; 562/435; 71/116, 115; 260/465 D

[56] References Cited

U.S. PATENT DOCUMENTS

T988,010  11/1979  Cunningham et al. ............... 560/21
3,686,266  8/1972  Krefeld et al. ......................... 560/21
3,979,437  9/1976  Theissen ................................. 560/21
4,193,790  3/1980  Rohr et al. ............................ 562/435
4,259,510  3/1981  Johnson ................................. 71/116

OTHER PUBLICATIONS

Morrison et al., "Org. Chemistry", pp. 344–352, Allyn & Bacon (1966).

Primary Examiner—James H. Reamer
Attorney, Agent, or Firm—Terence P. Strobaugh

[57]    ABSTRACT

A process for preparing a substantially pure, isomer free 5-(2-halo-4-trifluoromethylphenoxy)-2-nitrobenzoic acid or its esters, salts and amides by the basic condensation of a 4-trifluoromethylphenol and a 1-chloro-3-substituted-4-nitrobenzene followed by halogenation. All known previous routes afforded, in addition to the desired product, a number of inactive isomers.

5 Claims, No Drawings

PREPARATION OF 5-(2-HALO-4-TRIFLUOROMETHYLPHENOXY)-2-NITROBENZOIC ACID AND SALTS AND ESTERS AND AMIDES

This invention relates to a multi-step synthesis for preparing diphenyl ethers having the configuration which, at this time, is believed to afford the most active and selective herbicides known. This configuration is one where the diphenyl ether has a 4-trifluoromethyl substituent, a 2'-halo substituent and a 4'-nitro substituent.

The search for better and more economical methods for preparing these highly active herbicides is a continuing one. Some routes are described in U.S. Pat. Nos. 3,862,209; 4,031,131; and 4,262,152. Problems also exist in the stability of trifluoromethylphenol under basic conditions [See Jones, R. G., *J.A.C.S.*, 69, 2346-50 (1947)]. Therefore, a process which procedes at a rate to lessen the possible decomposition of trifluoromethylphenol and provide a substantially pure, isomer free compound is highly desirable.

Prior to this invention all processes for the preparation of these compounds afforded not only the desired active product, but also its isomers which are herbicidally inactive.

The presence of these inactive isomers creates problems in many areas: for example, in toxicological studies which are required for "impurities" in the active products.

A flow diagram for the process is as follows:

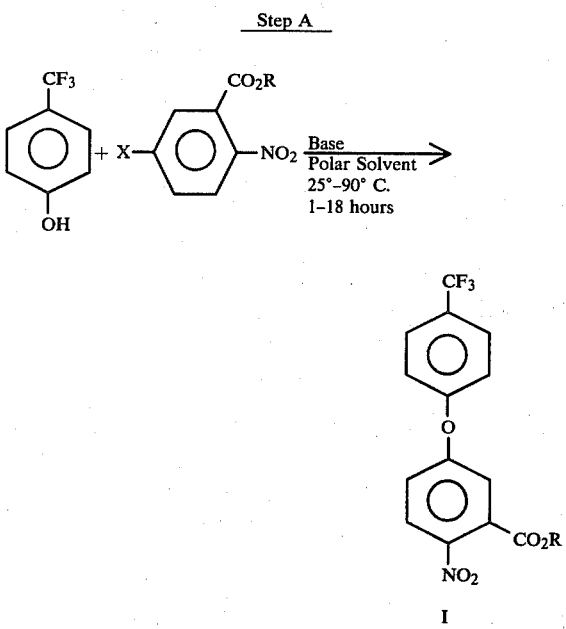

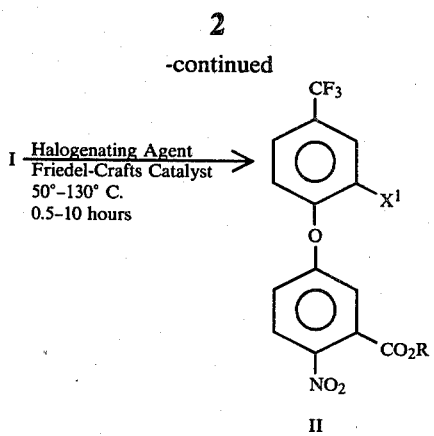

Step C (If desired)

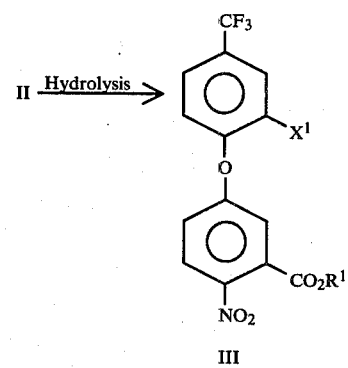

The condensation step, Step A, can employ inorganic bases such as sodium carbonate, potassium carbonate, sodium hydride, sodium hydroxide, potassium hydroxide, lithium hydroxide, Grignard reagents, lithium alkyls or any other base which will form the free anion of the phenol. The preferred base is potassium carbonate. This reaction is conducted using a polar solvent, such as, dimethyl sulfoxide, sulfolane, dimethylformamide, hexamethyl phosphoramide, tetramethylurea, tetramethylethylene diamine and the like. Dimethyl sulfoxide is the preferred solvent. The reaction is conducted at a temperature in the range of from about 25° to about 90° C. with the range of from about 50° to about 80° C. being more preferred and 70° C. being most preferred. The reaction is run for a period of time of from about 1 to about 18 hours with 2 to 3 hours being the normal time needed to complete the reaction.

Gas-liquid chromatography shows that only one product is obtained and yields of over 80% are obtained.

The halogenation step, Step B, affords, out of the five possible isomers, only the single desired product. While only chlorinating agents have been employed, it is believed that other halogenating agents would be equally effective such as fluoronating or iodonating agents.

Halogenating agents which can be employed include gaseous chlorine, sulfuryl chloride, N-chlorosuccinimide, tert-butyl hypochlorite, hydrogen chloride plus oxidizing agents (e.g. perchlorate) and the like with gaseous chlorine being the preferred chlorinating agent.

Friedel-Crafts catalysts may be employed such as ferric chloride, aluminum chloride and the like. The reaction may be conducted for a period of time of from 0.5 to 10 hours at a temperature in the range of from 50° to 130° C. The reaction is preferably run for no more than 3 hours at 70° C. A solvent may be employed although, in general, none is employed. Solvents which could be used include chlorinated solvents such as o-dichlorobenzene, perchloro ethylene or ethylene dichloride.

The product (II, supra) may be employed directly as a herbicide or may be converted to other herbicides by hydrolysis of the ester, salt or amide to the free acid which can be converted to other esters, alkali metal or alkaline earth metal salts or to various amine salts as desired.

The following is a description of the various substituents, X, $X^1$, R and $R^1$. X and $X^1$ are halo, for example, chloro, bromo, fluoro, or iodo.

R is hydrogen, alkyl, such as lower alkyl of from 1 to 5 carbon atoms, alkenyl, such as lower alkenyl of from 2 to 6 carbon atoms, alkynyl, such as lower alkynyl of from 2 to 6 carbon atoms, hydroxyalkyl such as hydroxy lower alkyl, carboxyalkyl such as carboxy lower alkyl, carbalkoxyalkyl, such as carbo lower alkoxy lower alkyl, cyanoalkyl such as, cyano lower alkyl, alkoxyalkyl, such as lower alkoxy lower alkyl, haloalkyl such as halo lower alkyl, a cation derived from an alkali metal or an alakline earth metal such as $Na^+$, $K^+$, $Li^+$, $Ca^{++}$, $Mg^{++}$, quaternary ammonium salts or amino, mono- and di- R aminos where R is as defined above. [Note: (1) When R is hydrogen, two equivalents of base must be employed; (2) R cannot be hydroxylmethyl; and (3) for the halogenation, R is preferably lower alkyl.]

The following examples illustrate this process:

EXAMPLE 1

5-(2-Chloro-4-trifluoromethylphenoxy)-2-nitrobenzoic acid and its Sodium Salt

Step A—Methyl 5-(4-trifluoromethylphenoxy)-2-nitrobenzoate p-Hydroxybenzotrifluoride (0.22 g, 1.36 mmol), powdered potassium carbonate (0.185 g, 1.34 mmol), and methyl 5-chloro-2-nitrobenzoate (0.288 g, 1.34 mmol) were heated at 70° C. under a nitrogen atmosphere in 3 ml of dimethyl sulfoxide. After 50 minutes, an aliquot was quenched in methanolic HCl. (By gas chromatography, the reaction is 45% complete.) After 18 hours (overnight), the reaction mixture was cooled to room temperature, diluted with water, and extracted with ether. The organic extracts are shaken with brine, dried ($MgSO_4$) and concentrated to afford methyl 5-(4-trifluoromethylphenoxy)-2-nitrobenzoate in 85% yield. Gas chromatography showed no starting phenol remained. Step B—Methyl 5-(2-chloro-4-trifluoromethylphenoxy) -2-nitrobenzoate Methyl 5-(4-trifluoromethylphenoxy)-2-nitrobenzoate is stirred with a catalytic amount of ferric chloride. The reaction mixture was heated to 70° C. under a continuous stream of chlorine gas. After 2.5 hours, the mixture was taken up in ether, shaken with water and the organic phase was dried over $MgSO_4$. The ether was evaporated to afford methyl 5-(2-chloro-4-trifluoromethylphenoxy)-2-nitrobenzoate. NMR ($CDCl_3$) $\delta$8.2–7 (m,6) 4.0 (2,3). TLC (40% ether/hexane) $R_f \approx .4$.

Step C—5-(2-Chloro-4-trifluoromethylphenoxy)-2-nitrobenzoic acid and its Sodium Salt Methyl 5-(2-chloro-4-trifluoromethylphenoxy)2-nitrobenzoate (0.06 mole) is dissolved in methanol (20 g) and a solution of 50% aqueous sodium hydroxide (0.120 mole) was added dropwise beginning at 25° C. The rate of addition is adjusted so as to control the exothermic reaction at less than or equal to 52° C. By this method the sodium salt of 5-(2-chloro-4-trifluoromethylphenoxy)-2-nitrobenzoic acid is generated in situ. Treatment with 6 M HCl to pH 1 in water (100 ml) afforded the free acid which was extracted into ethylene chloride. The ethylene chloride layer was decanted and concentrated under vacuum to afford 5-(2-chloro-4-trifluoromethylphenoxy)-2-nitrobenzoic acid.

By standard chemical methods 5-(2-chloro-4-trifluoromethylphenoxy)-2-nitrobenzoic acid can be converted to agronomically acceptable alkali and alkaline earth metal salts by reaction with one equivalent of an appropriate metal hydroxide or to agronomically acceptable amine salts by combining the acid with one equivalent of the appropriate amine. Solutions of the acid salts or free salts can be obtained depending upon reaction conditions. One method, not meant to be limiting but rather exemplatory, to isolate the sodium salt is described below.

EXAMPLE 1A

Sodium 5-(2-Chloro-4-trifluoromethylphenoxy)-2-nitrobenzoate 5-(2-Chloro-4-trifluoromethylphenoxy)-2-nitrobenzoic acid (3.0 g, 0.0083 mole) is dissolved in isopropyl alcohol (20 ml) and a solution of 50% aqueous sodium hydroxide (0.644 g, 0.0083 mole) is added dropwise and the reaction mixture stirred for 1 hour before removing the solvent and water under vacuum at 0.2 mm overnight to afford 2.8 g of sodium 5-(2-chloro-4-trifluoromethylphenoxy)-2-nitrobenzoate.

By following substantially the same procedure as described above the following compounds may be prepared:

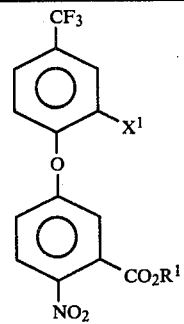

| EXAMPLE | $X^1$ | $R^1$ |
|---|---|---|
| 2 | Cl | $-C_2H_5$ |
| 3 | Cl | $-C_3H_7$ |
| 4 | F | $-CH_3$ |
| 5 | Br | $-CH_2CN$ |
| 6 | Cl | $-CH_2CH=CH_2$ |
| 7 | Cl | $-CH_2C\equiv CH$ |
| 8 | F | $-CH_2COOCH_3$ |
| 9 | Cl | $-CH_2COOH$ |
| 10 | Cl | $-CH_2CH_2Cl$ |
| 11 | Cl | $-CH_2OC_2H_5$ |
| 12 | Cl | $-N(C_2H_5)_2$ |
| 13 | Cl | $-K$ |
| 14 | Cl | $-CH(CH_3)CO_2CH_3$ |

What is claimed is:
1. A process for preparing substantially pure and isomer free compound of the formula:

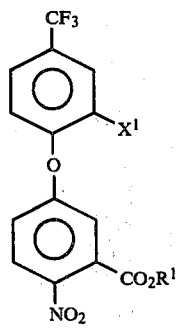

wherein $X^1$ is halo and $R^1$ is hydrogen, alkyl, alkenyl, alkynyl, hydroxyalkyl, carboxyalkyl, carbalkoxyalkyl, cyanoalkyl, alkoxyalkyl, haloalkyl, alkali metal or alkaline earth metal cations, quaternary ammonium cations, amino, mono- $R^1$ or di- $R^1$ amino wherein $R^1$ is as defined above which comprises reacting

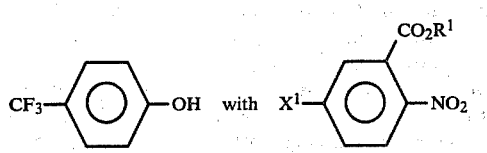

in the presence of an inorganic base in a polar solvent at a temperature in the range of from about 25° to 90° C. for from 1 to 18 hours to afford a substantially isomer free product of the formula:

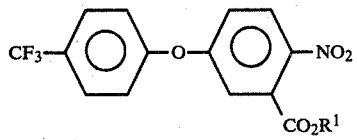

followed by treating said product with a halogenating agent in the presence of a Friedel-Crafts catalyst at at temperature in the range of from 50° to 130° C. for from 0.5 to 10 hours.

2. A process for preparing substantially pure and isomer free compound of the formula:

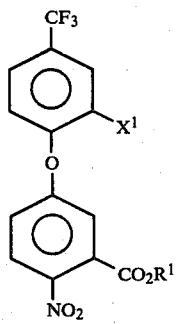

wherein $X^1$ is halo and $R^1$ is hydrogen, alkyl, alkenyl, alkynyl, hydroxyalkyl, carboxyalkyl, carbalkoxyalkyl, cyanoalkyl, alkoxyalkyl, haloalkyl, alkali metal or alkaline earth metal cations, quaternary ammonium cations, amino, mono- $R^1$ or di- $R^1$ amino wherein $R^1$ is as defined above which comprises reacting

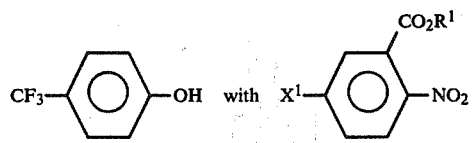

in the presence of an inorganic base in a polar solvent at a temperature in the range of from about 25° to 90° C. for from 1 to 18 hours to afford a substantially isomer free product of the formula:

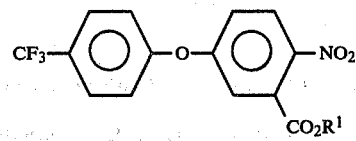

followed by treating said product with a halogenating agent in the presence of a Friedel-Crafts catalyst at at temperature in the range of from 50° to 130° C. for from 0.5 to 10 hours and hydrolyzing said product to the free acid.

3. A process for preparing substantially isomer free compound of the formula:

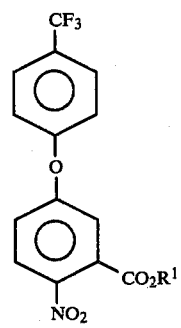

wherein $R'$ is hydrogen, alkyl, alkenyl, alkynyl, hydroxyalkyl, carboxyalkyl, carbalkoxyalkyl, cyanoalkyl, alkoxyalkyl, haloalkyl, alkali metal or alkaline earth metal cations, quaternary ammonium cations, amino, mono- $R^1$ or di- $R^1$ amino wherein $R^1$ is as defined above which comprises reacting

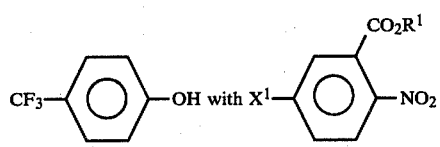

wherein $X'$ is halo, in the presence of an inorganic base in a polar solvent at a temperature in the range of from about 25° to 90° C. for from 1 to 18 hours to afford a substantially pure isomer free product.

4. A process for preparing a substantially pure isomer free product of the formula:

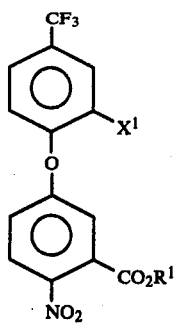

wherein X' is halo and R' is hydrogen, alkyl, alkenyl, alkynyl, hydroxyalkyl, carboxyalkyl, carbalkoxyalkyl, cyanoalkyl, alkoxyalkyl, haloalkyl, alkali metal or alakline earth metal cations, quaternary ammonium cations, amino, mono- $R^1$ or di- $R^1$ amino wherein $R^1$ is as defined above which comprises treating a compound of the formula:

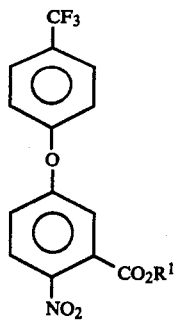

with a halogenating agent in the presence of a Friedel-Crafts catalyst at a temperature in the range of from 50° to 130° C. for from 0.5 to 10 hours.

5. A process for preparing 5-(2-chloro-4-trifluoromethylphenoxy)-2-nitrobenzoic acid and its sodium salt which comprises treating p-hydroxybenzotrifluoride with methyl 3-chloro-4-nitrobenzoate and potassium carbonate in dimethyl sulfoxide at about 70° C. for about 3 hours followed by treating the product obtained with chlorine gas in the presence of ferric chloride at about 70° C. for about 2.5 hours, hydrolyzing the ester with an aqueous base to obtain sodium 5-(2-chloro-4-trifluoromethylphenoxy)-2-nitrobenzoate which upon treatment with an inorganic acid affords 5-(2-chloro-4-trifluoromethylphenoxy)-2-nitrobenzoic acid.

* * * * *